United States Patent [19]

Bertossa

[11] 4,320,066

[45] Mar. 16, 1982

[54] PROCESS FOR THE PRODUCTION OF COBALTOCEN

[75] Inventor: Guiseppe Bertossa, Domat, Switzerland

[73] Assignee: Inventa AG fur Forschung und Patentverwertung Zurich, Zurich, Switzerland

[21] Appl. No.: 176,176

[22] Filed: Aug. 7, 1980

[30] Foreign Application Priority Data

Aug. 15, 1979 [CH] Switzerland ............................ 7469/79

[51] Int. Cl.$^3$ .............................................. C07F 15/06
[52] U.S. Cl. ............................................... 260/439 CY
[58] Field of Search ................................... 260/439 CY

[56] References Cited

U.S. PATENT DOCUMENTS

| 2,999,075 | 9/1961 | Pruett | 260/439 CY X |
| 3,088,961 | 5/1963 | Wilkinson | 260/439 CY |
| 3,450,728 | 6/1969 | Wilke et al. | 260/439 CY X |

*Primary Examiner*—Helen M. S. Sneed
*Attorney, Agent, or Firm*—Bierman & Bierman

[57] ABSTRACT

A process for the production of cobaltocen comprising reacting at least one cobalt alcoholate with cyclopentadiene in the presence of at least one alkaline catalyst is disclosed. The reaction product may be purified by various combinations of distillation, solution and filtration, and crystallization. Cobaltocen is a known compound useful as a catalyst and activator in various reactions.

16 Claims, No Drawings

PROCESS FOR THE PRODUCTION OF COBALTOCEN

This application claims the priority of Swiss No. 7469/79, filed Aug. 15, 1979.

The present application is directed to an improved process for the preparation of cobaltocen, otherwise known as bis-(cyclopentadientyl)-cobalt.

This is one of a large group which forms so-called "sandwich compounds" resulting from the reaction of a cyclopentadienyl anion with transition metals. Although such compounds consist of a bivalent metallic cation and two monovalent organic anions, they exhibit no salt-like characteristics, since their bonds are primarily covalent. As a result, their solutions do not dissociate ionically, and they can be sublimed at relatively low temperatures under a vacuum. Structural analyses of these compounds have shown that the rings of the cyclopentadienyl groups are superposed parallel to each other. The metal ion is clamped between them, whence comes the name "sandwich compound".

Cobaltocen, like many organic complexes of the transition metals, is an excellent catalyst. For example, U.S. Pat. No. 3,717,558 teaches the use of this compound as an activator for the photo polymerization of vinyl monomers. Japanese Pat. No. 4226/73 describes its use as a catalyst for the polymerization of acrylonitrile, especially where low molecular weight branched chains are desired. It has also been suggested as a catalyst for the hydration and isomerization of olefins.

One application which is of particular interest is as a catalyst for the synthesis of pyridine derivatives from alkynes and nitriles. (See Wokatsuki Y., Yamazuki M, Synthesis 1976, 26–8; and DOS No. 26 15 309). Cobaltocen is not the only catalyst that can be used in this reaction, since there are numerous cobalt compounds which have been suggested for this purpose. (See U.S. Pat. No. 4,006,149, and Boennemann, H., Brinkmann R., Schenklun H., Synthesis 1974, 575). However, when produced in accordance with the present invention, cobaltocen is the simplest and the cheapest of the various cobalt compounds which can act as a catalyst in the aforementioned reaction.

The preparation of cobaltocen has been described by various authors in the literature. For example, it can be directly synthesized from a finely divided cobalt metal and cyclopentadiene vapor. However, this method is very expensive because of the need for high temperatures and the resulting poor yields. The most common methods described up to now are based on the exchange reaction between an anhydrous cobalt salt and an alkali cyclopentadienyl. One of the most efficient methods is described by J. F. Cordes in Chem. Bu. 95,3084 (1962) and in German Pat. No. 1,206,897.

The foregoing methods require, at a preliminary stage, the preparation of an alkali cyclopentadienate. This is accomplished by reacting alkaline metals with cyclopentadiene. This step, particularly if the metals are in finely divided form, is always expensive, dangerous, and requires special precautions when attempted on a commercial scale. Other production methods using organo metallic compounds require even more operating steps and expensive chemicals.

The present invention is founded upon the discovery that cobalt alcoholates react directly with cyclopentadiene in the presence of alkaline reacting catalysts. Moreover, they produce cobaltocen in very good yields. The starting cobalt alcoholates are readily obtainable from the metal by electrolysis according to DOS No. 2,349,561. According to this patent, the cobalt is dissolved electrolytically in absolute alcohol by the addition of conducting salts. The alcoholate is obtained in powder form and can be used for the present process for the production of cobaltocen without the necessity of either purification or drying. However, since both the alcoholates and the cobaltocen are sensitive to air, all operations must be carried out in the absence of oxygen.

Suitable catalysts include the reaction products of alkali metals with weakly acid-reacting compounds. Similarly, the reaction products of alkali metals with alcohols and cyclopentadiene are also useful. In addition to the foregoing, ammonia and organic nitrogen bases are also useful in the present process.

The particular solvent used is not critical. It should dissolve the catalyst at least in small quantities and, of course, it should not react with the reactants or products to yield irreversible compounds. The choice is rather wide, and highly lipophilic petroleum fractions can be used, as can highly polar agents such as alcohols.

The educts and solvents must be free of water and oxygen before they are used. The reaction vessel must be kept oxygen free, as by rinsing with an inert gas. Argon has been found suitable for this purpose.

The reaction temperature and time can vary widely. They depend substantially on the activity of the particular catalyst, as well as on the type of solvent. In the case of ammonia, the heat of reaction must be eliminated at the start of the reaction by cooling in advance. This prevents the ammonia from evaporating. In most cases, heating is required in order to complete the reaction.

Purification of the end product can be effected in various ways. In one method, the volatile components are distilled off, and the cobaltocen is sublimed. In another method, the residue after distillation is dissolved in a solvent. This is preferably done in a hydrocarbon fraction at elevated temperature, followed by crystallization resulting from cooling.

The following Examples are intended to illustrate the invention.

EXAMPLE 1

149 grams (1 mole) of cobalt diethylate are suspended under exclusion of air in 1 liter of low boiling petroleum ether in a 2 liter flask which has previously been rinsed with argon. Then, 264 grams (4 moles) of freshly distilled cyclopentadiene and 20 ml of a solution of 50 grams of sodium cyclopentadienate in 1 liter of petroleum ether are added.

The solution is then gently boiled under reflux for 8 hours with constant stirring. Thereafter, the liquid components are distilled off in a vacuum, and the residue is dissolved in benzene. The benzene solution is filtered and evaporated to dryness. The residue is then dissolved in warm petroleum ether and crystallized by cooling. After the crystals have been filtered off and dried in a vacuum, 158 grams of black-violet crystals of approximately 2 mm are obtained. The cobalt content is 31.1%, which compares favorably with 31.16% which is the theoretical for cobaltocen.

EXAMPLE 2

500 cc of absolute alcohol are charged into a 1 liter flask which has been rinsed with argon. Prior to charging, the alcohol was freed of dissolved air by distillation under an argon atmosphere.

The alcohol is cooled to 0° C., and 140 grams of dry ammonia are introduced. 149 grams of cobalt diethylate are added in portions with stirring. The temperature then rises to room temperature. At that point, 145 grams of freshly distilled cyclopentadiene are added with vigorous stirring. The solution turns violet and thickly liquid, while the temperature rises by an additional 20° C. The stirring is continued for an additional half hour until the reaction mass returns to room temperature. The liquid components are evaporated under vacuum, and the residue is sublimed at a pressure of 0.2 millibar 155 grams of pure cobaltocen are obtained.

EXAMPLE 3

The same method was carried out as in Example 2, but the residue is dissolved, after distillation, in warm petroleum ether and crystallized by cooling to 30° C. A finely crystalline cobaltocen is obtained. The mother liquor is concentrated to about one third by distillation, and recrystallized so that a second portion of cobaltocen is obtained. The two portions yielded a total of 161 grams.

EXAMPLE 4

35 grams of cobalt ethanolate, 28 grams diethylamine, and 36.5 grams of freshly distilled cyclopentadiene are boiled in 250 cc of anhydrous toluene under argon for 16 hours at 78° C. under reflux. After cooling, the liquid components are vacuum distilled off. The solid residue is boiled with petroleum ether. The ether is then filtered while hot and kept for 14 hours at 50° C. Cobaltocen crystallizes in fine dark violet crystals, which are filtered off and dried in a vacuum. The yield is 23.1 grams (52% of theoretical) based on cobalt ethanolate. The empirical analysis is as follows:

|          |    | Found | Theoretical |
|----------|----|-------|-------------|
| Analysis | Co | 30.90 | 31.16       |
|          | C  | 64.01 | 63.51       |
|          | H  | 5.07  | 5.33        |

While only a limited number of specific embodiments of the present invention have been expressly disclosed, it is, nonetheless, to be broadly construed and not to be limited except by the character of the claims appended hereto.

I claim:

1. A process for the production of cobaltocen comprising reacting, in the absence of oxygen and under anhydrous conditions, at least one cobalt alcoholate with cyclopentadiene in the presence of at least one alkaline catalyst taken from the class consisting of alkali metal alcoholates, alkali metal phenolates, alkali metal cyclopentadienates, ammonia, and organic nitrogen bases.

2. The process of claim 1 wherein said catalyst is alkali metal cyclopentadienate.

3. The process of claim 1 wherein said reaction is carried out under anhydrous conditions.

4. The process of claim 1 wherein said reaction is carried out in the absence of oxygen.

5. The process of claim 1 wherein said catalyst is ammonia.

6. The process of claim 1 wherein said catalyst is an amine.

7. The process of claim 1 wherein said reaction is carried out above room temperature.

8. The process of claim 1 wherein said catalyst is a reaction product of an alkali metal with a weakly acid compound.

9. The process of claim 1 wherein a solvent is present, said solvent dissolving at least some of said catalyst and yielding no irreversible compounds with any products of said reaction.

10. The process of claim 1 wherein said cobaltocen is purified by distilling off any volatile components and subliming said cobaltocen.

11. The process of claim 1 wherein said cobaltocen is purified by distilling off any volatile components to form a first residue, dissolving said first residue in a solvent therefor, and crystallizing out said cobaltocen.

12. The process of claim 11 wherein said solvent is a hydrocarbon fraction and said dissolving takes place at elevated temperatures.

13. The process of claim 12 wherein said residue is dissolved in said solvent to form a solution, said solution is filtered and evaporated to dryness to form a second residue, dissolving said second residue in said hydrocarbon fraction at an elevated temperature, and crystallizing out said cobaltocen.

14. The process of claim 1 wherein alcoholate is cobalt diethylate.

15. The process of claim 1 wherein said catalyst is taken from the class consisting of sodium cyclopentadienate, ammonia, and diethylamine.

16. The process according to claim 9 wherein said solvent is taken from the class consisting of low boiling petroleum ether and absolute alcohol.

* * * * *